United States Patent
Bennis et al.

(10) Patent No.: US 6,716,884 B1
(45) Date of Patent: Apr. 6, 2004

(54) PHARMACEUTICAL COMPOSITIONS FOR ORAL ADMINISTRATION OF PHLOROGLUCINOL AND PREPARATION THEREOF

(75) Inventors: Abderrahim Bennis, Casablanca (MA); Jean-Jacques Serrano, Montpellier (FR); Farid Bennis, Casablanca (MA)

(73) Assignee: Promindus (Actions Promotionnelles Dans l'Industrie et le Commerce), Casablanca (MA)

( * ) Notice: Subject to any disclaimer, the term of this patent is extended or adjusted under 35 U.S.C. 154(b) by 0 days.

(21) Appl. No.: 09/926,534

(22) PCT Filed: May 19, 2000

(86) PCT No.: PCT/FR00/01365

§ 371 (c)(1),
(2), (4) Date: Jan. 22, 2002

(87) PCT Pub. No.: WO00/71110

PCT Pub. Date: Nov. 30, 2000

(51) Int. Cl.$^7$ .................. A61K 31/05; A61K 31/045; A61K 31/60; A61K 09/46; A61K 09/20

(52) U.S. Cl. ............... 514/734; 514/739; 514/159; 514/819; 424/55; 424/464; 424/466; 424/43; 424/678; 424/681; 424/679; 424/686

(58) Field of Search .................. 514/734, 739, 514/159, 819; 424/55, 464, 466, 43, 678, 681, 679, 686

(56) References Cited

U.S. PATENT DOCUMENTS 3,607,271 A * 9/1971 Hilhorst et al. ............. 430/149

FOREIGN PATENT DOCUMENTS

| EP | 643962 | 3/1995 |
| FR | 784 M | 9/1961 |
| FR | 2722408 | 1/1996 |
| GB | 904955 | * 12/1959 |
| GB | 1227744 | 4/1971 |
| WO | 92/02209 | 2/1992 |
| WO | 97/17064 | 5/1997 |

OTHER PUBLICATIONS

Kotz & Treichel, Chemistry & Chemical Reactivity, Third Edition, pp. 860–861.*
Bayer Bitterfeld GmbH, Alka–Seltzer, Almanya, Mar. 18, 1991, Registration number: 90/21.*
Ole Daniel Enersen, Tyrode's Solution.*

* cited by examiner

*Primary Examiner*—Dwayne C. Jones
*Assistant Examiner*—Clinton T. Ostruop
(74) *Attorney, Agent, or Firm*—Dennison, Schultz, Dougherty & MacDonald

(57) ABSTRACT

A pharmaceutical composition for the administration of phloroglucinol includes phloroglucinol in combination with a buffer system capable of buffering the composition when placed in an aqueous medium to a pH between 3 and 7.

28 Claims, No Drawings

PHARMACEUTICAL COMPOSITIONS FOR ORAL ADMINISTRATION OF PHLOROGLUCINOL AND PREPARATION THEREOF

BACKGROUND OF THE INVENTION

The present invention relates to pharmaceutical compositions for the oral administration of phloroglucinol (1,3,5-trihydroxybenzene) and to the preparation thereof. Said compositions, which are novel, are of value inasmuch as the antispasmodic activity of the phloroglucinol (antispasmodic activity on the smooth muscle fibers) is potentiated in these compositions.

Said antispasmodic activity of said phloroglucinol has been known since 1961 (reference may be made in particular to Debray et al., THERAPIE, 1961, 16, pages 978 to 990, and Cahen et al., THERAPIE, 1962, page 17). Thus phloroglucinol is used in the treatment of spasmodic and painful manifestations of the urinary tract, the hepatic ducts, the digestive tract and the gynecological apparatus. At the present time, it is administered orally in the form of tablets or lyophilizates, rectally in the form of suppositories, or by injection (i.m. or i.v.). Lyophilizates are generally preferred for oral administration in as much as they exhibit a more rapid and more complete bioavailability than tablets. Said lyophilizates are active more rapidly. The customary oral dose of phloroglucinol is generally 160 mg, taken as two tablets or lyophilizates.

SUMMARY OF THE INVENTION

In such a context, the Applicant now proposes a novel galenical form for the oral administration of said phloroglucinol. Said novel galenical form can come in a number of variants. It can be novel per se (cf., for example, the effervescent tablets, granules or powders described further in the present text) or it can consist of a modified conventional galenical form (cf., for example, the tablets or lyophilizates described further in the present text). Whatever its form of presentation, said galenical form is characteristically buffered to a pH of between 3 and 7.

According to its main subject, the present invention thus relates to pharmaceutical compositions for the oral administration of phloroglucinol, characterized in that, when liquid, they contain a system which buffers them to a pH of between 3 and 7, or in that, when solid, they contain a system which, when they are placed in an aqueous medium, is capable of exerting a buffer effect between pH 3 and pH 7.

DETAILED DESCRIPTION OF THE INVENTION

The composition of the pharmaceutical compositions of the invention is characteristically such that it exerts a buffer effect in the pH range mentioned above, said range being delimited by said values pH 3 and pH 7 inclusive. Said buffer effect in said pH range ($3 \leq pH \leq 7$) is of course compatible with the stability of the active principle in question, namely phloroglucinol (this compound, which is oxidizable in alkaline media, must not in fact be exposed to pH values of >7); it makes it possible to reduce the gastric acidity and, totally surprisingly, it potentiates the antispasmodic activity of said phloroglucinol. Effervescent tablets buffered as defined by the invention have thus proved almost as effective as an intramuscular injection, and oral lyophilizates buffered as defined by the invention have also proved more effective than the oral lyophilizates of the prior art (non-buffered).

Advantageously, the pharmaceutical compositions of the invention are buffered to a pH of between 4 and 6 ($4 \leq pH \leq 6$).

It has already been seen above that said pharmaceutical compositions, buffered as defined by the invention, can exist in various forms. In particular, they can be presented in liquid forms (directly buffered to an appropriate pH) such as solutions, suspensions or syrups, or in solid forms (which will develop the buffer effect in a liquid, generally water, when they are taken, or in the stomach after they have been taken) such as tablets (effervescent or non-effervescent, advantageously effervescent, cf. below), gelatin capsules, powders (effervescent or non-effervescent, advantageously effervescent, cf. below), granules (effervescent or non-effervescent, advantageously effervescent, cf. below) or lyophilizates. This is not an exhaustive list.

Those skilled in the art who are specialized in galenics will in any case know how to formulate phloroglucinol, especially in one or other of the unit forms listed above, with an appropriate system responsible for the desired buffer effect. Such unit forms (for example tablets, especially conventional tablets, double-core tablets, effervescent tablets) obviously and advantageously constitute the essence of the pharmaceutical compositions of the invention. However, pharmaceutical compositions containing at least two separate components (on the one hand a component containing at least the active principle, and on the other hand another component containing at least the system generating the desired buffer effect), said separate components being intended for simultaneous administration, cannot be totally excluded from the framework of the invention.

Within the framework of a preferred embodiment of the invention, said system responsible for the buffer effect comprises at least one organic acid and/or at least one salt of an organic acid in association with at least one strong base and/or at least one salt of a strong base.

Within the framework of this preferred embodiment, said organic acid is advantageously selected from citric, tartaric, malic, lactic, acetic, glutaric, benzoic and adipic acids and/or said base takes the form of sodium bicarbonate, sodium carbonate, calcium carbonate, magnesium carbonate, sodium hydroxide, potassium hydroxide, potassium bicarbonate or potassium carbonate.

Particularly advantageously, the pharmaceutical compositions of the invention consist of effervescent solid galenical forms; they are presented especially in the form of effervescent tablets, effervescent granules or effervescent powders. Within the framework of this advantageous variant, the same system is generally and opportunely responsible for the desired buffer effect and the effervescence.

According to the invention, effervescent phloroglucinol tablets are very particularly preferred. Such tablets have proved more effective than the oral lyophilizates of the prior art and, in addition, they are less expensive to manufacture than said oral lyophilizates.

Such tablets are capable of containing the above-defined associations of organic acid(s) and/or organic acid salt(s) with strong base(s) and/or strong base salt(s). Advantageously, they contain the combination citric acid/sodium bicarbonate.

It is therefore to the inventors' credit to have established that the above-specified buffer effect potentiates the antispasmodic activity of phloroglucinol and to propose novel galenical forms of said phloroglucinol with potentiated antispasmodic activity, especially effervescent forms.

The preparation of the pharmaceutical compositions of the invention, as described above, constitutes the second subject of said invention. Said preparation is that of a buffered galenical form. Characteristically, it comprises formulating the phloroglucinol in the liquid form with a system which buffers said liquid form to a pH of between 3 and 7 (advantageously of between 4 and 6), or in the solid form with a system which, when said solid form is placed in an aqueous medium, is capable of exerting a buffer effect between pH 3 and pH 7 (advantageously between pH 4 and pH 6).

It has already been indicated that said preparation should not present any problems whatsoever for those skilled in the art who are specialized in galenics.

On a point of information, it is proposed to specify below, purely by way of illustration, an advantageous procedure for the preparation of effervescent phloroglucinol tablets.

First of all, the active principle, phloroglucinol dihydrate, is mixed with the system responsible for both the effervescence and the desired buffer effect, namely citric acid+ sodium bicarbonate. Small amounts of additives, such as a lubricant (for example sodium benzoate) and/or a preservative and/or a sweetener (for example sucrose sodium), etc., are advantageously added to said mixture.

The resulting mixture of powders is sieved and then granulated with an aqueous-alcoholic solvent. The granules obtained are successively dried and graded. Their residual moisture content is then checked. Finally, they are lubricated and then compressed for agglomeration into tablet form. Said tablets are then packed in their primary packaging.

This process for the manufacture of effervescent tablets is not novel per se. The novelty derives from the fact that it is carried out with phloroglucinol.

Purely by way of illustration, the composition by weight of an effervescent tablet of the invention can also be specified below:

| | |
|---|---|
| Phloroglucinol (dihydrate) | 80.0 mg |
| Citric acid | 297.2 mg |
| Sodium bicarbonate | 362.6 mg |
| Sodium benzoate | 15.2 mg |

When dissolved in a glass of water, such a tablet generates a solution buffered to pH 4.5.

Finally, it is proposed to illustrate the value of the present invention by means of the following presentation of comparative results of pharmacological tests.

In said tests, the antispasmodic activity of different galenical forms of phloroglucinol was evaluated using the SIEGMUND test. The principle of this test, which is familiar to those skilled in the art, is summarized below.

The pain syndrome caused in mice by the intraperitoneal injection of 0.25 ml of a phenylbenzoquinone solution is characterized by stretching movements of the back paws and twisting movements of the dorso-abdominal musculature, which are counted over a period of 30 min, starting 15 min after the administration of said phenylbenzoquinone. An antispasmodic effect is represented by a reduction in the number of these movements. For each test, the test substance is administered intragastrically, or by some other route, 30 min before the administration of said phenylbenzoquinone.

A first study was performed on three groups of mice.

An effervescent tablet of the invention containing 80 mg of phloroglucinol, was dissolved in distilled water so that a dose of 100 mg/kg was administered in a volume of 20 ml/kg via an esophageal tube (Group A of the invention).

The controls (Group B) received the same volume of distilled water.

An aqueous solution containing the same dose was prepared from oral lyophilizates (Lyoc) of the prior art. It was administered under the same conditions (Group C).

The results obtained were expressed as the percentage protection against the spasms induced by phenylbenzoquinone, relative to the controls. They are indicated below:

Group [A] C: Lyoc: 28% (not significant relative to the controls (Group B))

Group [C] A: Effervescent compound: 47% (significant at p>0.001)

The antispasmodic activity exhibited by the effervescent tablet is appreciably greater than that of the oral lyophilizate.

Under similar and obviously comparative conditions, said percentage inhibition of the spasms relative to a control group was evaluated at different doses (40 mg/kg, 80 mg/kg and 160 mg/kg) of phloroglucinol (dihydrate) formulated as:

an oral lyophilizate: LYOC (prior art)

an injectable solution: I.M. (prior art)

an effervescent tablet: EFFERV. (invention)

a buffered oral lyophilizate: LYOC' (invention)

In this fourth case, a device was in fact implemented. A lyophilizate of the prior art (LYOC) was dissolved in distilled water and buffered to pH 5 with citric acid and sodium bicarbonate (LYOC').

The results obtained are expressed as above in the following Table:

| | Percentage inhibition of spasms | | |
|---|---|---|---|
| | 40 mg/kg | 80 mg/kg | 160 mg/kg |
| LYOC | 6 | 24 | 34* |
| I.M. | 12 | 43*** | 59*** |
| EFFERV. | 20 | 43*** | 53*** |
| LYOC' | | | 45*** |

*p = 0.05
***p = 0.001

A statistical analysis performed between LYOC and I.M. or EFFERV. at the 80 mg dose shows a highly significant difference: p=0.001.

A statistical analysis performed between LYOC and I.M. or EFFERV. at the 160 mg dose shows a highly significant difference: p=0.01.

A statistical analysis performed between I.M. and EFFERV. at the 160 mg dose shows that the difference is not significant.

A statistical analysis performed between LYOC and LYOC' at the 160 mg dose shows a statistically significant difference: p=0.05.

A statistical analysis performed between EFFERV. and LYOC' at the 160 mg dose shows that the difference is not significant.

The data in said table leave no doubt as to the value of the present invention.

What is claimed is:

1. A solid pharmaceutical composition for oral administration of phloroglucinol, comprising solid phloroglucinol in combination with a solid buffer system which is sufficient to buffer gastric acidity to a pH between pH 3 and pH 7.

2. A solid pharmaceutical composition according to claim 1, wherein said pH is between 4 and 6.

3. A solid pharmaceutical composition according to claim 1, in the form of tablets, gelatin capsules, powders, granules or lyophilizates.

4. A solid pharmaceutical composition according to claim 1, in the form of an effervescent solid galenical preparation.

5. Process for the preparation of a solid pharmaceutical composition according to claim 1, comprising formulating the phloroglucinol in a solid form with a solid buffer system sufficient to buffer gastric acidity to a pH between pH 3 and pH 7.

6. A solid pharmaceutical composition according to claim 1, in the form of an effervescent tablet.

7. A solid pharmaceutical composition according to claim 6, in the form of an effervescent tablet containing citric acid and sodium bicarbonate.

8. A solid pharmaceutical composition according to claim 1, wherein said buffer system comprises at least one organic acid and/or at least one salt of an organic acid in association with at least one strong base and/or at least one salt of a strong base.

9. A solid pharmaceutical composition according to claim 8, wherein said organic acid is selected from the group consisting of citric, tartaric, malic, lactic, acetic, glutaric, benzoic and adipic acids.

10. A solid pharmaceutical composition according to claim 8, wherein said base comprises sodium bicarbonate, sodium carbonate, calcium carbonate, magnesium carbonate, sodium hydroxide, potassium hydroxide, potassium bicarbonate or potassium carbonate.

11. A method for administration of phloroglucinol to a human or animal in need thereof, comprising formulating the phloroglucinol in a composition in combination with a buffer system capable of buffering gastric acidity to a pH between 3 and 7, and administering the composition to a human or animal.

12. The method of claim 11, wherein the pH is between 4 and 6.

13. The method of claim 11, wherein the phloroglucinol is formulated in a solid composition.

14. The method of claim 11, wherein the phloroglucinol is formulated in a liquid composition.

15. The method of claim 11, wherein the composition is administered in liquid form.

16. The method of claim 15, wherein the liquid form in effervescent.

17. The method of claim 11, wherein the composition is administered in solid form.

18. The method of claim 17, wherein the solid form is a tablet or gelatin capsule.

19. The method of claim 11, wherein said buffer system comprises at least one organic acid and/or at least one salt of an organic acid in association with at least one strong base and/or at least one salt of a strong base.

20. The method of claim 19, wherein said organic acid is selected from the group consisting of citric, tartaric, malic, lactic, acetic, glutaric, benzoic and adipic acids.

21. The method of claim 19, wherein said base comprises sodium bicarbonate, sodium carbonate, calcium carbonate, magnesium carbonate, sodium hydroxide, potassium hydroxide, potassium bicarbonate or potassium carbonate.

22. A dosage form for pharmaceutical administration of phloroglucinol, comprising a therapeutically effective amount of phloroglucinol in combination with a buffer system which is capable of buffering gastric acidity to a pH of between 3 and 7.

23. The dosage form of claim 22, which is a tablet or gelatin capsule.

24. The dosage form of claim 22, which is an effervescent tablet or granules.

25. The dosage form of claim 22, which is in the form of a liquid.

26. The dosage form of claim 22, wherein the therapeutically effective amount is about 80 mg.

27. The dosage form of claim 22 wherein the buffer is capable of maintaining a pH of between 4 and 6.

28. The dosage form of claim 27, wherein the buffer system comprises citric acid and sodium bicarbonate.

* * * * *